US00PP16229P2

(12) United States Plant Patent

Ramming et al.

(10) Patent No.: US PP16,229 P2

(45) Date of Patent: Jan. 31, 2006

(54) GRAPEVINE DENOMINATED 'SCARLET ROYAL'

(50) Latin Name: *Vitis vinifera*
Varietal Denomination: Scarlet Royal

(75) Inventors: David W. Ramming, Fresno, CA (US); Ronald E. Tarailo, Fresno, CA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 140 days.

(21) Appl. No.: 10/953,124

(22) Filed: Sep. 28, 2004

(51) Int. Cl.
*A01H 5/00* (2006.01)

(52) U.S. Cl. ..... Plt./205

(58) Field of Classification Search ..... Plt./205
See application file for complete search history.

(56) References Cited

PUBLICATIONS

Bryant, D. New table grapes presented. Western Farm Press, Mar. 17, 2001 [retrieved on Apr. 21, 2005]. Retrieved from the Internet: <http://westernfarm press.com/mag/arming_new_table_grapes/>.*

Ramming, D., "USDA Grape Breeding Program and Promising Experimental Selections," San Joaquin Valley Table Grape Seminar, Feb. 21, 2001 Visalia, CA.

Ramming, D. et al., "Development of Seedless Grapes for the Fresh Market—1999," 1999–00 Viticulture Research Report, California Table Grape Commission (1999) vol. XXVIII.

Ramming, D. et al., "Development of Seedless Grapes for the Fresh Market Including Types Resistance to Powdery Mildew—2000," 2000–01 Viticulture Research Report, California Table Grape Commission (2000) vol. XXIX.

Ramming, D. et al., "Development of Seedless Grapes for the Fresh Market Including Types Resistance to Powdery Mildew—2001," 2001–02 Viticulture Research Report, California Table Grape Commission (2001) vol. XXX.

Ramming, D. et al., "Development of Seedless Grapes for the Fresh Market Including Types Resistance to Powdery Mildew—2002," 2002–03 Viticulture Research Report, California Table Grape Commission (2002) vol. XXXI.

Ramming, D. et al., "Development of Seedless Grapes for the Fresh Market Including Types Resistance to Powdery Mildew—2003," 2003–04 Viticulture Research Report, California Table Grape Commission (2003) vol. XXXII.

* cited by examiner

*Primary Examiner*—Anne Marie Grunberg
*Assistant Examiner*—June Hwu
(74) *Attorney, Agent, or Firm*—Margaret A. Connor; John D. Fado; Leslie Shaw

(57) ABSTRACT

A new and distinct variety of grapevine denominated 'Scarlet Royal' which is characterized by its mid-season ripening seedless fruit, attractive dark red coloration, its oval fruit shape, its firm fruit texture with neutral sweet flavor, and its medium dense cluster.

2 Drawing Sheets

Latin name of the genus and species of the plant claimed: *Vitis vinifera* L.

Variety denominated: 'Scarlet Royal'.

BACKGROUND OF THE INVENTION

The present invention relates to a new and distinct variety of grapevine, *Vitis vinifera* L., which will hereinafter be denominated varietally as the 'Scarlet Royal' grapevine, and, more particularly, to a grapevine which has fruit maturing for commercial harvesting and shipment approximately August 15 in the San Joaquin Valley of central California. The fruit has an attractive dark red skin coloration at maturity with oval shape seedless berries.

The grapevine of the present invention originated from a hand-pollinated cross of United States Department of Agriculture selection 'C33-30' (unpatented) and the United States Department of Agriculture selection 'C51-63' (unpatented) made in 1992 at the United States Department of Agriculture, Agricultural Research Service, Postharvest Quality and Genetics Research Unit plots at California State University, Fresno, in Fresno, Calif. The female was 'C33-30', a seedless, red-fruited grapevine with reflex anthers in the flower, large oval berries with firm flesh and medium skin, and a neutral flavor. The fruit of the 'C33-30' ripen about two weeks after the instant variety. The pollen parent was 'C51-63' a seedless red-purple fruited grape with medium size, oval to elliptical berries with good skin and firm flesh. The fruit of the 'C51-63' grapevine ripen four weeks after the variety of the subject invention. Both of the parents of the instant cultivar are hybrids of the grapevine genus and species *Vitis vinifera* L.

The aborted seeds resulting from this controlled hybridization were developed further through in vitro tissue culture and germinated in the laboratory during the fall of 1992. The resulting seedling population totaled 21 individual plants. All seedlings were planted in the spring of 1993 in a vineyard at the United States Department of Agriculture, Agricultural Research Service plots on the California State University, Fresno, campus in Fresno, Calif. The seedlings fruited in the summer of 1995 and one, the grapevine of the present invention, was designated as 'B34-82' and selected for its attractive dark red seedless, firm, large berry size, and outstanding fruit quality.

In 1996 at the inventors' direction, the grapevine of the subject invention was propagated asexually by rooting hardwood cuttings at Fresno, Calif. and a test planting of two grapevines of the subject invention was established in the United States Department of Agriculture, Agricultural Research Service plots on the California State University, Fresno campus. Subsequently in 1997 a larger test planting of 24 vines was established with rooted hardwood cuttings of the instant invention. The instant cultivar rooted readily from hardwood cuttings. All grapevines of the new variety planted from hardwood cutting propagation, fruited in the third season of growth after planting. All propagules, or resulting plants, of the present invention have been observed by the inventors to be true to type in that all asexual reproduced grapevines of the variety possessed the characteristics identical to those of the original parent grapevine.

SUMMARY OF THE INVENTION

The grapevines of the subject invention possess medium vigor and have produced fruit as own-rooted grapevines. The size of the grapevines was determined by growing the grapevines on a three cross arm 'T' type trellis structure with a top cross arm of 122 cm in length set 189 cm above the ground; a second cross arm of 102 cm in length set 156 cm above the ground; and a third cross arm 91 cm in length set 125 cm above the ground. The trellis structure had two wires per cross arm and indicated a grapevine height of 199 cm and a grapevine spread of 179 cm.

The fruit of the new variety ripens in midseason, about the same time as the 'Ruby Seedless' grapevine (unpatented). The average ripening date in Fresno, Calif. is August 15. Berries adhere very well to the fruit pedicel and have minimal shatter from the clusters during storage. The fruit is dark red in color at maturity. The fruit shape is oval. Fruit skins are thick compared to medium thick skins for 'Ruby Seedless' grapevine. The pulp of the fruit adheres to the skins of the berry and the fruit texture is firm and meaty. The berries are medium in size, or 5.8 grams. The flavor of the fruit is sweet and has been rated high. Soluble solids concentration of the juice at fruit maturity averages 22.0% with titratable acid of 0.55 grams/100 milliliters of juice. The fruit is of the stenospermocarpic type of seedlessness and contains small, aborted seed traces that are not noticeable when eaten. The fruit clusters are usually borne on the average of 0.56 per shoot on spur pruned vines. The fruit clusters are conical and are large in size, or 835 grams, medium density and attractive. The fruit cluster peduncles are medium in length.

The grapevine and fruit of the new variety are susceptible to powdery mildew disease of grape plants. A spray program for powdery mildew disease control is required.

BRIEF DESCRIPTION OF THE DRAWINGS

The drawings of the grapevine of the present invention are color photographs showing in FIG. 1 a typical specimen of the fruit and in FIG. 2 a shoot with leaves and a flower cluster all of the new variety of the present invention.

The color of the photographs is as nearly true as it is reasonably possible to provide in such color photographs. Description of the new invention applies to vines of 'Scarlet Royal' grown on its own roots at a density of 1,119 vines per hectare in Fresno County, Calif. in 2002. These vines were in their third year of full production having been planted in 1997.

DETAILED BOTANICAL DESCRIPTION

Figure 1:
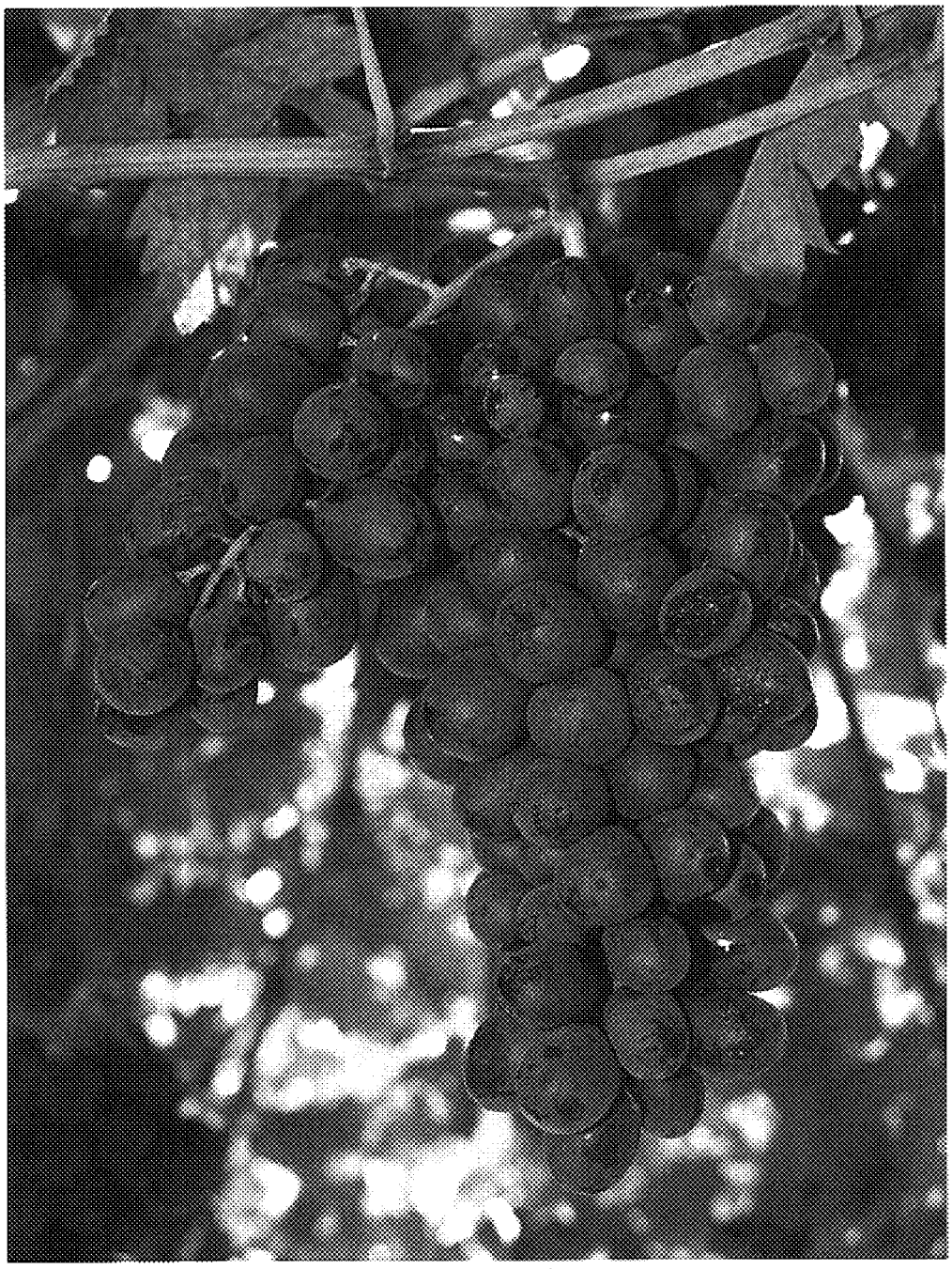
Figure 2:
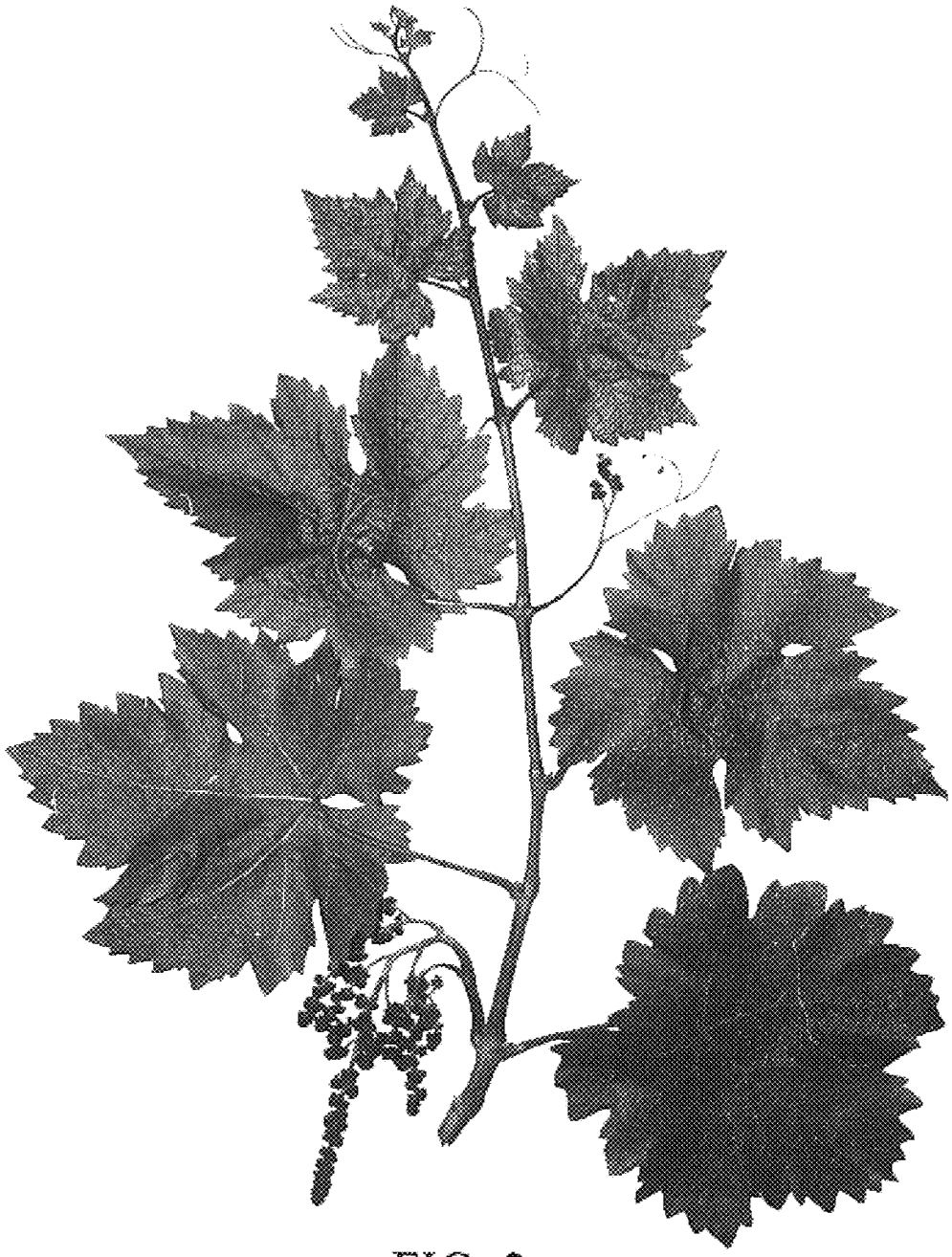

The new variety cv. 'Scarlet Royal' may be distinguished from other commercial grape cultivars known to us by a combination of characteristics, including its mid-season ripening seedless fruit with easy to develop attractive dark red coloration, its firm fruit texture with a neutral sweet flavor, its oval fruit shape, large berry size and its medium density cluster.

The new variety of grapevine is most similar to its pollen parent 'C51-63' by having dark red, firm texture fruit. It is distinguished therefrom and an improvement thereon in a number of fruit characteristics. The berry size is larger, and the dark red color is easier to develop. The fruit ripens 4 weeks before 'C51-63'. The new grapevine is also similar to the commercial variety 'Ruby Seedless' in that they ripen at the same time and have red seedless berries. It is distinguished therefrom and an improvement thereon in that the berries of the new variety are larger and firmer than those of 'Ruby Seedless'. It is also similar to the commercial variety 'Crimson Seedless' (unpatented), in that they have firm red seedless fruit. It is distinguished therefrom and an improvement thereon in that the berries of the new variety are larger and develop the dark red color easier than does 'Crimson Seedless'.

The new variety also differs substantially from its mother parent 'C33-30'. The new variety has perfect flowers with functional male and female parts while 'C33-30' has only functional female parts. The most distinguishing difference is the thicker skin, firmer berries that develop dark red color easily, while 'C33-30' has thin skin, medium firm berries that do not develop red color easily.

Referring more specifically to the botanical details of this new and distinct variety of grapevine, the following has been observed under the ecological conditions prevailing at the orchard of origin which is located in Fresno in the San Joaquin Valley of central California. All major color code designations are by reference to the *Dictionary of Color,* by Maerz and Paul, First Edition, 1930. Common color names are also occasionally employed. Where dimensions, sizes, colors and other characteristics are given, it is to be understood that such characteristics are approximations of averages set forth as accurately as practicable. The description hereof was taken from specimens grown in Fresno, Calif. The grapevines used for measurement were grown in a fine sandy loam soil and the grapevines were irrigated using trickle, or drip irrigation. In a substantial part, the data hereof was from grapevines that were six (6) years old.

VINE

Generally:

*Size.*—Medium. Grapevine size as determined on grapevines growing on a three cross arm 'T' trellis with the top cross arm 122 cm long set 189 cm above the ground; the second cross arm 102 cm long set 156 cm above the ground; and the third cross arm 91 cm long set 125 cm above the ground. There were two wires per cross arm and was trained to produce a grapevine height of 200 cm and a grapevine spread of 199 cm.

*Vigor.*—Medium vigor. Vigor as measured by weighing prunings at dormant pruning for spur pruned grapevines (with 34 spurs and 2 buds per spur) was 5.96 Kg.

*Productivity.*—Productive, 31.2 Kg per grapevine on grapevines spaced 8 ft. (243.84 cm) by 12 ft. (365.76 cm).

*Regularity of bearing.*—Regular. Annual pruning is required for reliable production.

CANES

*Size.*—Diameter — Mature Canes — Medium diameter, medium vigor, upright in growth habit. Mature Canes — Diameter — Internode Base — 10.4 mm. Mature Canes — Diameter — Internode Midpoint — 8.9 mm. Mature Canes — Diameter — Internode Tip — 4.5 mm. Mature Canes — Diameter — Node Base — 12.5 mm. Mature Canes — Diameter — Node Midpoint — 10.4 mm. Mature Canes — Diameter — Node Tip — 6.1 mm.

*Internode length.*—Base — 8.5 cm. Internode Length — Midpoint — 9.4 cm. Internode Length — Tip — 6.4 cm.

*Average length of canes.*—233.6 cm.

*Surface texture.*—Smooth.

*Color of mature cane.*—Orange brown (plant 14 E7). No anthocyanin observed on mature canes.

*Buds.*—Color — Brown (plate 8 L6). Buds — Texture — Smooth.

*Dormant bud* (*compound bud or eye*).—Width — At base of cane 5.1 mm; at midpoint of cane 6.1 mm and at tip of cane 4.3 mm. The average number of buds on a current, single-season growth cane is 29.

*Date of bud break.*—March 29, late season.

*Young shoots.*—Young shoots have cobwebby indument.

*Diameter of young shoots in spring* (*measured when shoots are 24 inches*).—At base 8.3 mm, at midpoint 7.1 mm and at tip 4.5 mm.

*Internode length.*—5.3 cm at $4^{th}$ internode from base.

*Young shoots.*—Color — Pale green (plate 21 L6) with very slight red on edge.

*Stem of shoot tip.*—Color — Green (plate 21 L9) with ½ to ¾ covered with red streaks (plate 46 L6) on the sun exposed side.

*Shoot.*—Shape — Straight to slightly curved.

*Shoot tip.*—Form — Open.

*Tendrils.*—Size — Length — 22.5 cm. Tendrils — Size — Diameter — 2.39 mm. Tendrils — Shape — Usually biforcated or triforcated and curled on distal end. Tendrils — Pattern — Found beginning opposite node 7 and 8, then again at nodes 10, 11, 13, 14, 16, 17 with this repeating intermittent pattern to the distal end of the cane. Tendril — Color Immature Growth — Yellow green (plate 20 L7) with dark red streaks (plate 46 L6).

*Disease resistance.*—Susceptible to powdery mildew, and fungicides were applied to the grapevines under evaluation to control powdery mildew.

*Insect resistance.*—Insecticides were applied to the grapevines under evaluation to control grapevine leafhoppers and variegated leafhoppers. No resistances to these pests were determined in these evaluations due to chemical control of these pests.

LEAVES

*Size.*—Generally — Leaves simple and alternate. The mid vein (L1) is 13.3 cm long, vein L2 is 12.0 cm long and vein L3 is 9.2 cm long. The angle between the mid vein L1 and L3 is 106 degrees and between L1 and the 1st vein off L3 is 151 degrees.

*Average length.*—18.7 cm.

*Average width.*—18.2 cm.

*Shape.*—Orbicular.

*Lobes.*—Number — Five (5).

*Color.*—Upwardly Disposed Surface — Dark green (plate 23 L7). Upward surface is glabrous, flat and smooth to slightly bullate. Color — Downwardly Disposed Surface — Green (plate 23 L6). Lower surface is glabrous with medium amount of very few short erect hairs along the main midrib vein.

*Leaf vein.*—Color — Light green (plate 19 K3) with no red pigment on veins of leaf. Leaf Vein — Thickness — Thickness of mid vein at center of leaf is 1.7 mm.

*Leaf margin.*—Serrated with shape of teeth pointed and medium to large in size.

*Petiole sinus.*—Lyre shape and usually petiole lobes are half open. On mature leaf is 3.5 cm deep and 1.47 cm wide at widest point.

*Petiole.*—Size — Medium. Petiole — Length — 16.3 cm. Petiole — Diameter — 2.8 mm. Petiole — Color — Green (plate 20 J5) with 50% to 90% red (plate 4 G2) covering.

*Young leaf.*—Color — Upper Surface — Green (plate 21 L6) with copper over color and cobwebby indument on upper surface. Young leaf — Color — Lower Surface — Green (plate 20 I6). Young leaf — Shape unfolded — Concave.

*Petiole of young leaf.*—Color — Green (plate 22 L8).

*Stipules.*—Onion skin.

TRUNK

*Size.*—Medium. Size — Height — Approximately 104 cm above the vineyard floor. Size — Diameter — 6.7 cm as measured just below the cordon or head point at 81.28 cm above vineyard floor; and 6.8 cm at 15.2 cm above the vineyard floor.

*Bark.*—Color — (plate 15 C4).

FLOWERS

*Flower.*—Size — Generally — Medium. Flower — Unopened — Diameter — 2.2 mm. Flower — Unopened — Length — 3.1 mm. Flower — Unopened — Surface Texture — Smooth.

*Date of bloom.*—First bloom May 6, 2002.

*Date of full bloom.*—May 13, 2002 at 90%.

*Inflorescence.*—Panicle.

*Cluster size.*—At Bloom — Generally, medium. Cluster — Length — 15.3 cm. Cluster — Width — 13.7 cm.

*Peduncle.*—Length — 4.1 cm.

*Shape of cluster.*—Conical with well developed shoulders.

*Calyptra.*—Color — Green (plate 20 K7).

*Stamens.*—Five (5) and erect.

*Pistil.*—Well developed.

*Ovary.*—Color — Green (plate 20 L7).

*Pollen.*—Normal, fertile, abundant.

*Anthers.*—Color — Light yellow (plate 9 J1).

FRUIT

Maturity when described: Ripe for commercial harvesting and shipment approximately August 15 in Fresno, Calif. Mid-season with 'Ruby Seedless' grapevine.

Cluster:
*Size.*—Spur Pruned Vines — 835 grams.
*Length.*—23.8 cm.
*Width.*—18.5 cm.
*Shape.*—Conical.
*Density.*—Medium, on average has 144 berries per cluster.
*Clusters per vine.*—48, spur pruned.
*Clusters per shoot.*—0.56 clusters per shoot.

Peduncle:
*Size.*—Length — Medium, 5.5 cm. Size — Diameter — Medium, 5.8 mm.
*Color.*—Green (plate 20 H6).
*Texture.*—Smooth, glabrous.

Pedicel: Generally — There is good attachment between the berry and the pedicel.
*Size.*—Length — 8.1 mm. Size — Diameter — 2.0 mm.
*Color.*—Green (plate 20 F7).
*Texture.*—Glabrous with a few lenticels.
*Brush.*—Length — 3.0 mm. Brush color — Green (plate 20 D3).

Berry:
*Size.*—Medium, avg. 5.8 grams.
*Shape.*—Oval.
*Length.*—2.43 cm.
*Width.*—1.79 cm.
*Color.*—Dark red (plate 6 L6).
*Bloom.*—Medium.

Skin: Generally — The skin adheres to the flesh.
*Thickness.*—Medium to thick in thickness.
*Texture.*—Smooth.
*Tendency to crack.*—None.

Flesh:
*Flesh color.*—Translucent and very pale yellow green (plate 19 I2).
*Texture.*—Firm, meaty.
*Juice production.*—Medium.
*Color of juice.*—Clear.
*Flavor.*—Sweet and acid, neutral flavor.
*Soluble solids.*—22.0%.
*Titratable acid.*—0.55 g/100 ml juice.
*Aroma.*—None.
*Ripening.*—Uniform.
*Eating quality.*—Very good, sweet.

Character of seeds: Stenospermocarpic seedless, small aborted seed traces that are not noticeable when eaten. Average aborted seed trace when present are 12.5 mg fresh weight, 5.6 mm long and 1.9 mm wide. Seed color is gray (plate 7 A1).

Use: Fresh market. No wine nor raisin evaluations have been done.

Keeping quality: Very good.

Resistance to disease: No resistance to powdery mildew.

Shipping and handling qualities: Berries ship and handle similar to Thompson Seedless except there is less berry shatter.

Although the new variety of grapevine possesses the described characteristics noted above as a result of the growing conditions prevailing in Fresno, Calif. in the central San Joaquin Valley of California, United States of America, it is to be understood that variations of the usual magnitude and characteristics incident to changes in growing conditions, training, irrigation, fertilization, pruning, pest control, climatic variation and the like are to be expected.

Having thus described and illustrated our new variety of grapevine, what we claim as new and desire to be secured by Plant Letters Patent is:

1. A new and distinct variety of grapevine plant, 'Scarlet Royal', substantially as illustrated and described, characterized by its attractive dark red fruit color, oval fruit shape, and firm flesh texture with a neutral sweet flavor.

* * * * *